United States Patent [19]

Brown et al.

[11] Patent Number: 5,525,355
[45] Date of Patent: Jun. 11, 1996

[54] LAXATIVE COMPOSITIONS

[75] Inventors: Adrian Brown; Sandra T. A. Malkowska; Stewart T. Leslie; Derek A. Prater, all of Cambridge, England; Ronald B. Miller, Basel, Switzerland

[73] Assignee: Euro-Celtique, S.A., Luxembourg, Luxembourg

[21] Appl. No.: 304,396

[22] Filed: Sep. 12, 1994

[30] Foreign Application Priority Data

Sep. 14, 1993 [GB] United Kingdom .................. 9318950

[51] Int. Cl.$^6$ .................................................. A61K 9/64
[52] U.S. Cl. .......................................... 424/456; 424/451
[58] Field of Search ................................ 424/451, 456, 424/400, 478, 195.1, 480

[56] References Cited

U.S. PATENT DOCUMENTS

| | | | |
|---|---|---|---|
| 4,321,263 | 3/1982 | Powell et al. | 424/195 |
| 4,324,779 | 4/1982 | Dahlhausen et al. | 424/20 |
| 4,810,707 | 3/1989 | Michaelson | 514/277 |
| 4,828,842 | 5/1989 | Furst et al. | 242/480 |
| 4,861,591 | 8/1989 | Weierstall et al. | 424/690 |
| 5,167,959 | 12/1992 | Chicouri | 424/400 |

FOREIGN PATENT DOCUMENTS

| | | | |
|---|---|---|---|
| 0001822 | 5/1979 | European Pat. Off. | A61K 9/48 |
| 0011237 | 5/1980 | European Pat. Off. | A61K 31/765 |
| 0068450 | 1/1983 | European Pat. Off. | A61K 9/20 |
| 0086468 | 8/1983 | European Pat. Off. | A61K 31/64 |
| 0095123 | 11/1983 | European Pat. Off. | A61K 9/26 |
| 0103290 | 3/1984 | European Pat. Off. | A61K 31/765 |
| 0122463 | 10/1984 | European Pat. Off. | A61K 9/48 |
| 0049852 | 8/1985 | European Pat. Off. | A61K 9/48 |
| 0173293 | 3/1986 | European Pat. Off. | A61K 31/445 |
| 0223369 | 5/1987 | European Pat. Off. | A61K 31/19 |
| 0222614 | 5/1987 | European Pat. Off. | A61K 9/66 |
| 0243930 | 11/1987 | European Pat. Off. | A61K 9/52 |
| 0274870 | 7/1988 | European Pat. Off. | A61K 9/10 |
| 0276116 | 7/1988 | European Pat. Off. | A61K 9/48 |
| 0299668 | 1/1989 | European Pat. Off. | A61K 31/19 |
| 0308943 | 3/1989 | European Pat. Off. | A61K 31/12 |
| 0343575 | 11/1989 | European Pat. Off. | A61K 9/48 |
| 0349509 | 1/1990 | European Pat. Off. | A61K 47/00 |
| 0369445 | 5/1990 | European Pat. Off. | A61K 9/48 |
| 0374359 | 6/1990 | European Pat. Off. | A61K 9/48 |
| 0228417 | 8/1990 | European Pat. Off. | A61K 9/48 |
| 0398287 | 11/1990 | European Pat. Off. | A61K 9/08 |
| 0403748 | 12/1990 | European Pat. Off. | A61K 9/20 |
| 0455396 | 11/1991 | European Pat. Off. | A61K 9/06 |
| 0462066 | 12/1991 | European Pat. Off. | A61K 31/19 |
| 0464274 | 1/1992 | European Pat. Off. | A61K 9/48 |
| 0496705 | 7/1992 | European Pat. Off. | A61K 9/48 |
| 0502554 | 9/1992 | European Pat. Off. | A61K 37/50 |
| 0520888 | 12/1992 | European Pat. Off. | A61K 31/765 |
| 0413171 | 5/1993 | European Pat. Off. | A61K 31/485 |
| 0580860 | 2/1994 | European Pat. Off. | A61K 9/14 |
| 0368247 | 6/1994 | European Pat. Off. | A61K 9/26 |
| 1591573 | 6/1970 | France . | |
| 3438830 | 4/1986 | Germany | A61K 31/44 |
| 3636123 | 5/1988 | Germany | A61K 31/44 |
| 298351 | 2/1992 | Germany | A61K 9/48 |
| 7800268 | 7/1979 | Netherlands | A61K 47/00 |
| 7806048 | 12/1979 | Netherlands | A61K 47/00 |
| 680620 | 1/1968 | South Africa . | |
| 1212119 | 11/1970 | United Kingdom | A61K 19/08 |
| 1302471 | 1/1973 | United Kingdom | A61K 9/00 |
| 1481323 | 7/1977 | United Kingdom | A61K 33/08 |
| 1516653 | 7/1978 | United Kingdom | A61K 33/18 |
| 1604622 | 12/1981 | United Kingdom | A61K 31/765 |
| 2155889 | 10/1985 | United Kingdom | A61K 9/48 |
| 2145627 | 7/1986 | United Kingdom | A61K 31/765 |
| 2142824 | 2/1987 | United Kingdom | A61K 9/20 |
| 2160100 | 6/1989 | United Kingdom | A61K 9/22 |
| 2222770 | 3/1990 | United Kingdom | A61K 9/10 |
| WO8604503 | 8/1986 | WIPO | A61K 31/12 |
| WO8700754 | 2/1987 | WIPO | A61K 31/765 |
| WO8806038 | 8/1988 | WIPO | A61K 31/77 |
| WO9007336 | 7/1990 | WIPO | A61K 31/74 |
| WO9014073 | 11/1990 | WIPO | A61K 9/08 |
| WO9102520 | 3/1991 | WIPO | A61K 9/48 |
| WO9218106 | 10/1992 | WIPO | A61K 9/14 |
| WO9300101 | 1/1993 | WIPO | A61K 31/765 |
| WO9315745 | 8/1993 | WIPO | A61K 31/77 |
| WO9323022 | 11/1993 | WIPO | A61K 31/12 |
| WO9325212 | 12/1993 | WIPO | A61K 31/765 |

OTHER PUBLICATIONS

European Search Report of European Application No. EP 94 30 6086.
Examiner's Report to the Comptroller under Section 17 (The Search report) of British Application No. GB 9410103.7.
James E. F. Reynolds, *Martindale, The Extra Pharmacopoeia*, The Pharmaceutical Press (1989); p. 1088.
British National Formulary, No. 25, *Danthron*, British Medical Association and Royal Pharmaceutical Society of Great Britain;p. 41, Mar. 1993.
Examiner's report to the Comptroller under Section 17 (The Search report) of Application No. GB 9318950.4.
J. Connaughton, C. F. McCarthy, *Comparison of Combination of Ispaghula/Ploxamer 188 and Placebo on Gastointestinal Transit Time*, Irish Medical Journal, Mar. 1982, vol. 75, No. 3, pp. 93–94.
James E. F. Reynolds, *Danthron*, Martindale, The Extra Pharmacopoeia, The Pharmaceutical Press 1982, p. 1364.
Chemical Abstract, CA117(6):5603r.

*Primary Examiner*—Thurman K. Page
*Assistant Examiner*—William E. Benston, Jr.
*Attorney, Agent, or Firm*—Steinberg, Raskin & Davidson

[57] ABSTRACT

A method for the manufacture of a laxative composition in dosage unit form which comprises the steps of melting a normally solid stool softener; dispersing and/or dissolving a stimulant laxative compound in the molten stool softener and mixing to obtain a uniform mixture; filling the molten dispersion into hard gelatin capsule shells; and allowing the capsules to cool and the melt or dispersion to solidify.

14 Claims, No Drawings

LAXATIVE COMPOSITIONS

BACKGROUND OF THE INVENTION

This invention is concerned with improvements in and relating to laxative compositions and the manufacture thereof.

Orally administrable compositions containing a stool softener in combination with a stimulant laxative are known and such compositions may, for example, take the form of suspensions containing the active ingredients in appropriate liquid carriers for oral administration.

It has now been found, in accordance with the present invention, that a surprisingly high dose of a laxative composition can be incorporated in a small size of hard gelatin capsule by dispersing and dissolving the stimulant laxative in molten stool softener and filling the resultant molten dispersion into capsules. The resultant composition thus provides an unexpectedly high unit dose of the laxative composition in a pharmaceutical form which and shape for elegant, convenient and reliable administration to patients.

Conventionally a unit dosage form is prepared by compressing powders into tablets or encapsulating powders into hard gelatin capsules. To achieve satisfactory powder flow and either compression or encapsulation properties, it is conventionally necessary to formulate a product with excipients such as diluents, compression aids, binders, flow aids and lubricants. This is especially true when one or more of the active ingredients has undesirable physicochemical properties, for example is waxy and/or sticky, which make incorporating the ingredient in a conventional dosage form particularly difficult. Furthermore to ensure that the resulting dosage unit will break up and dissolve after administration it is usually necessary to add a disintegrant. These excipient materials add considerably to the volume of the dosage form, and may limit the amount of active ingredient(g) which may be incorporated in a unit dosage form of acceptable size and volume to ensure acceptance by a patient.

SUMMARY OF THE INVENTION

According to the invention, therefore, there is provided a method for the manufacture of a laxative composition in dosage unit form which comprises the steps of:

(i) melting a normally solid stool softener;

(ii) dispersing a stimulant laxative compound in the molten stool softener and mixing to achieve a uniform mixture;

(iii) filling the molten dispersion into hard gelatin capsule shells; and (iv) allowing the capsules to cool and the molten dispersion to solidify therein.

The method of the invention makes it possible to manufacture a laxative composition in dosage unit form without the use of excipients or other adjuvants and, further, makes it possible to obtain an unexpectedly high dose in a preparation of small physical sizes.

DETAILED DESCRIPTION

Suitable stimulant laxatives for use in the compositions produced in accordance with the invention include Danthron (1,8-dihydroxyanthraquinone), Bisacodyl, Casanthranol, Cascara, Sennosides and sodium picosulphate. Of these, Danthron is particularly preferred.

By the term "normally solid", as applied to the stool softening agent we mean a material which is solid at ambient temperatures, e.g. 20° to 25° C. In order to provide the desired melt, in which the stimulant laxative is dispersed, the stool softener suitably has a melting point of from 30° to 90° C., preferably 40° to 80° C. as measured after addition of the stimulant laxative, and any minor additives, which may lower the solidification or melting point. Examples of suitable stool softeners include the so-called Poloxamers (polyoxyethylene-polyoxypropylene block copolymers) especially Poloxamer 188. Poloxamer 188 is the preferred stool softening agent for use in accordance with the invention. Other pharmaceutically acceptable stool softening laxatives may be suitable for use in accordance with the invention provided their melting point, after incorporation of the stimulant laxative, is from 30° to 90° C.

The weight ratio of stool softener to stimulant laxative will vary depending upon the specific nature of the two components and the desired intended effect. When the stool softener is Poloxamer 188 and the stimulant laxative is Danthron the weight ratio of stool softener to stimulant laxative is suitably from 2:1 to 20:1, preferably from 4:1 to 15:1 and most preferably from 8:1 to 13.3:1.

The compositions to be filled into the capsules, in accordance with the invention, are simply prepared by melting the stool softener and maintaining its temperature at the desired level, in a jacketed stainless steel mixing vessel. The stimulant laxative is dispersed in the molten stool softener by mixing and homogenization until a uniform dispersion is obtained. The molten dispersion is then filled into gelatin capsules and the capsules cooled.

It should be understood that to obtain an unexpectedly high dose in a preparation of small physical size it is particularly advantageous if all or part of the stimulant laxative dissolves in the molten stool softener. For example danthron will dissolve in poloxamer 188 to the extent of approximately 2% w/w at 60° C. and approximately 3% w/w at 80° C. Thus for a preparation containing 500 mg of poloxamer 188 and 37.5 mg danthron prepared according to the invention, approximately 40% (15 mg) of the danthron will be dissolved in the poloxamer at 80° C. For a preparation containing 200 mg poloxamer 188 and 25 mg of danthron approximately 24% (6 mg) of the danthron will be dissolved in the poloxamer at 80° C. This enables the size of the resulting dosage form to be minimized.

EXAMPLES

In order that the invention may be well understood the following Examples and Comparative Examples are given by way of illustration only.

EXAMPLE 1

Co-danthramer Capsule 25 mg/200 mg

|  | mg/Capsule |
|---|---|
| Danthron B.P. | 25.0 |
| Poloxamer 188 U.S.N.F. | 200 |
| Total | 225 |

Melt the poloxamer 188 in a jacketed stainless steel mixing vessel and maintain the temperature at 60° to 80° C. Add the danthron with vigorous mixing and homogenization and continue mixing and homogenizing until a uniform solution/dispersion is obtained. Fill the molten dispersion into size 3 hard gelatin capsules (volume 0.3 ml) using a capsule filling machine equipped for liquid filling of capsules, for example a Bosch 1500L machine.

The density of the contents of the capsule shell, prepared according to the present invention, is approximately 0.84 g/ml. Therefore by preparing capsules according to the invention the normal dose of co-danthramer can be achieved by administering one or two size 3 capsules as the volume of the preparation has been minimized by achieving a high density.

It is further surprising that capsules prepared according to the invention and without any excipients to aid manufacture or disintegration exhibit excellent uniformity of danthron content and satisfactory dissolution rate of the danthron as shown below:

| Time during encapsulation run | Danthron content (mg/capsule) | Coefficient of Variation (%) |
|---|---|---|
| Start | 24.7 | 2.45 |
| Middle | 24.9 | 1.90 |
| End | 24.6 | 1.82 |

| Time (minutes) | Danthron Dissolved (%) |
|---|---|
| 10 | 18 |
| 20 | 48 |
| 30 | 73 |
| 45 | 95 |

EXAMPLE 2

Strong Co-danthramer Capsule 37.5 mg/500 mg

|  | mg/Capsule |
|---|---|
| Danthron B.P. | 37.5 |
| Poloxamer 188 U.S.N.F. | 500 |
| Total | 537.5 |

Melt the poloxamer 188 in a jacketed stainless shell mixing vessel and maintain the temperature at 60° to 80° C. Add the danthron with vigorous mixing and homogenization and continue mixing and homogenizing until a uniform solution/dispersion is obtained. Fill the molten dispersion into size 0 hard gelatin capsule (volume 0.68 ml) using a capsule filling machine equipped for liquid filling of capsules, for example a Bosch 1500OL machine.

The density of the contents of the capsule shell, prepared according to the present invention, is approximately 0.98 g/ml. Therefore by preparing capsules according to the invention the normal dose of strong co-danthramer can be achieved by administering one or two size 0 capsules as the volume of the preparation has been minimized by achieving a high density.

It is further surprising that capsules prepared according to the invention and without any excipients to aid manufacture or disintegration exhibit excellent uniformity of danthron content and satisfactory dissolution rate of the danthron as shown below:

| Time during encapsulation run | Danthron content (mg/capsule) | Coefficient of Variation (%) |
|---|---|---|
| Start | 36.9 | 0.96 |
| Middle | 36.2 | 1.36 |
| End | 37.2 | 2.25 |

| Time (minutes) | Danthron Dissolved (%) |
|---|---|
| 10 | 14 |
| 20 | 38 |
| 30 | 59 |
| 45 | 83 |

Comparative Example 3

Co-danthramer Capsule 25 mg/200 mg

|  | mg/Capsule |
|---|---|
| Danthron B.P. | 25.0 |
| Poloxamer 188 U.S.N.F. | 200 |
| Total | 225 |

Blend powdered poloxamer 188 and the danthron in a mixer until a uniform blend is obtained. Fill powder into size 1 hard gelatin capsule (volume 0.5 ml). The density of the contents of the capsule shell, prepared according to the comparative example is approximately 0.45 g/ml. Therefore by preparing capsules by conventional powder filling the normal dose of co-danthramer can only be achieved by administering one or two size 1 capsules even in the absence of excipients which would be required to enable the powder blend to be filled on a high speed capsule filling machine.

Comparative Example 4

Strong Co-danthramer Capsule 37.5 mg/500 mg

|  | mg/capsule |
|---|---|
| Danthron B.P. | 37.5 |
| Poloxamer 188 U.S.N.F. | 500 |
| Total | 537.5 |

Blend powdered poloxamer 188 and the danthron in a mixer until a uniform blend is obtained. Fill powder blend into size 000 hard gelatin capsule (volume 1.37 ml). The density of the contents of the capsule shell, prepared according to the comparative example is approximately 0.45 g/ml. Therefore by preparing capsules by conventional powder filling the normal dose of strong co-danthramer can only be achieved by administering one or two size 000 capsules even in the absence of excipients which would be required to enable the powder blend to be filled on a high speed capsule filling machine. Size 000 capsules are generally regarded as too large for human administration, being utilized for large animal veterinary applications and use of smaller size 0 capsules would necessitate administration of two or four capsules to achieve the normal dose of strong co-danthramer.

Thus it was found that conventional methods of formulation of a stimulant laxative, danthron, and a stool softener, poloxamer 188 yielded an unacceptably large dosage form even before addition of the excipients necessary to allow commercial manufacture.

Preparation of capsules according to the invention, therefore, allows for the manufacture of a laxative composition in unit dosage form without addition of any excipients or other adjuvant and which furthermore minimizes the volume of the active ingredients to enable achievement of an unexpectedly high dose in a preparation of small physical size.

What is claimed is:

1. A method for the manufacture of a laxative composition in dosage unit form which comprises the steps of:
   (i) melting a normally solid stool softener;
   (ii) dispersing and/or dissolving a stimulant laxative selected from the group consisting of danthron, bisacodyl, casanthranol, cascara, a sennoside, sodium picosulphate, and mixtures thereof in the molten stool softener and mixing to obtain a uniform mixture;
   (iii) filling the molten dispersion into hard gelatin capsule shells:
   (iv) allowing the capsules to cool and the melt or dispersion to solidify.

2. A method as claimed in claim 1 in which the stool softener has a melting point from 30° to 90° C., preferably 40° to 80° C., when measured after addition of the stimulant laxative and/or other minor additive which may lower the melting or re-solidification point; and the stimulant laxative is Danthron, Bisacodyl, Casanthranol, Cascara, a Sennoside or sodium picosulphate.

3. A method as claimed in claim 2 in which the stool softener is a poloxamer and the stimulant laxative is Danthron.

4. A method as claimed in claim 3 in which the weight ratio of poloxamer to danthron is between 2:1 and 20:1, preferably between 4:1 and 15:1 and most preferably between 8:1 and 13.3:1.

5. A method as claimed in claim 1 wherein said stimulant laxative compound is danthron and said normally solid stool softener is Poloxamer 188, and wherein said capsule provides a danthron dissolution rate where 18% by weight of danthron is dissolved after 10 minutes, 48% by weight danthron is dissolved after 20 minutes, 73% by weight danthron is dissolved after 30 minutes, and 95% by weight danthron is dissolved after 45 minutes.

6. The product prepared by the method of claim 4.

7. A method for the manufacture of a combination stool softener/stimulant laxative unit dosage form, comprising:
   (i) melting ambiant stool softener which is solid at ambiant temperatures;
   (ii) dispersing and/or dissolving a stimulant laxative selected from the group consisting of danthron, bisacodyl, casanthranol, cascara, a sennoside, sodium picosulphate, and mixtures thereof in the molten stool softener, and mixing the same to obtain a molten dispersion having a ratio of stool softener to stimulant laxative is from 2:1 to 20:1,
   (iii) filling said molten dispersion into hard gelatin capsules; and
   (iv) cooling said capsules to obtain a final product.

8. The method of claim 7, wherein said molten dispersion has a density from about 0.84 g/ml to about 0.98 g/ml.

9. The method of claim 8, wherein said hard gelatin capsule shells have a volume of 0.3 ml.

10. The method of claim 9, wherein said stool softener is included in said unit dosage form in an amount of about 200 mg/capsule, and said stimulant laxative is present in an amount of about 25 mg/capsule.

11. The method of claim 9, wherein said stool softener is present in the amount of about 500 mg/capsule and said stimulant laxative is provided in the amount of about 37.5 mg/capsule, and wherein said hard gelatin capsule shells have a volume of about 0.68 ml.

12. A unit dose of a combination stool softener/stimulant laxative unit dosage form, comprising:
   a hard gelatin capsule, wherein said capsule is filled with a mixture consisting of a solid mixture of a stool softener and a stimulant laxative; wherein said stool softener is a poloxamer and said stimulant laxative is selected from the group consisting of danthron, bisacodyl, casanthranol, cascara, sennoside, sodium picosulphate, and mixtures thereof, wherein said stool softener is melted and said stimulant laxative is dispersed or dissolved in said molten stool softener and mixed to obtain a uniform mixture; and wherein said uniform mixture is filled into hard gelatin capsule shells; wherein the ratio of said stool softener to said stimulant laxative is from about 2:1 to about 20:1.

13. The unit dosage form of claim 12, wherein said stool softener is included in the amount of about 500 mg/capsule and wherein said stimulant laxative is danthron and is included in the amount of about 37.5 mg/capsule.

14. A laxative capsule comprising: from about 25 mg danthron and about 200 mg poloxamer, wherein said poloxamer is melted, said danthron is dispersed in said melted poloxamer to obtain a uniform mixture of molten dispersion, and wherein hard gelatin capsules are filled with said molten dispersion and cooled.

* * * * *